United States Patent
Malhotra et al.

(10) Patent No.: US 11,379,717 B2
(45) Date of Patent: Jul. 5, 2022

(54) SYSTEMS AND METHODS FOR CLASSIFICATION OF MULTI-DIMENSIONAL TIME SERIES OF PARAMETERS

(71) Applicant: Tata Consultancy Services Limited, Mumbai (IN)

(72) Inventors: Pankaj Malhotra, Noida (IN); Priyanka Gupta, Noida (IN); Lovekesh Vig, Gurgaon (IN); Gautam Shroff, Gurgaon (IN)

(73) Assignee: Tata Consultancy Services Limited, Mumbai (IN)

( * ) Notice: Subject to any disclaimer, the term of this patent is extended or adjusted under 35 U.S.C. 154(b) by 772 days.

(21) Appl. No.: 16/363,038

(22) Filed: Mar. 25, 2019

(65) Prior Publication Data
US 2020/0012938 A1   Jan. 9, 2020

(30) Foreign Application Priority Data
Jul. 9, 2018  (IN) .............................. 201821025603

(51) Int. Cl.
*G06N 3/08* (2006.01)
*G06F 16/28* (2019.01)

(52) U.S. Cl.
CPC ............. *G06N 3/08* (2013.01); *G06F 16/285* (2019.01)

(58) Field of Classification Search
CPC ................................. G06N 3/08; G06F 16/285
See application file for complete search history.

(56) References Cited

U.S. PATENT DOCUMENTS

| | | | |
|---|---|---|---|
| 6,063,028 A | 5/2000 | Luciano | |
| 10,616,253 B2* | 4/2020 | Hagi | G06N 5/041 |
| 2011/0106743 A1* | 5/2011 | Duchon | G06F 16/35 |
| | | | 706/46 |
| 2011/0224565 A1 | 9/2011 | Ong et al. | |
| 2012/0108997 A1 | 5/2012 | Guan et al. | |
| 2019/0147300 A1* | 5/2019 | Bathen | G06N 3/0454 |
| | | | 706/12 |

* cited by examiner

*Primary Examiner* — Minh Chau Nguyen
(74) *Attorney, Agent, or Firm* — Finnegan, Henderson, Farabow, Garrett & Dunner, LLP

(57) ABSTRACT

Traditional systems and methods have implemented hand-crafted feature extraction from varying length time series that results in complexity and requires domain knowledge. Building classification models requires large labeled data and is computationally expensive. Embodiments of the present disclosure implement learning models for classification tasks in multi-dimensional time series by performing feature extraction from entity's parameters via unsupervised encoder and build a non-temporal linear classifier model. A fixed-dimensional feature vector is outputted using a pre-trained unsupervised encoder, which acts as off-the shelf feature extractor. Extracted features are concatenated to learn a non-temporal linear classification model and weight is assigned to each extracted feature during learning which helps to determine relevant parameters for each class. Mapping from parameters to target class is considered while constraining the linear model to use only subset of large number of features.

12 Claims, 7 Drawing Sheets

SYSTEMS AND METHODS FOR CLASSIFICATION OF MULTI-DIMENSIONAL TIME SERIES OF PARAMETERS

PRIORITY CLAIM

This U.S. patent application claims priority under 35 U.S.C. § 119 to India Application No. 201821025603, filed on Jul. 9, 2018. The entire contents of the aforementioned application are incorporated herein by reference.

TECHNICAL FIELD

The disclosure herein generally relates to time series analysis, and, more particularly, to systems and methods for classification of multi-dimensional time series of parameters.

BACKGROUND

There has been a growing interest in using deep learning models for various clinical prediction tasks from Electronic Health Records (HER), for medical diagnosis, to predict future diseases in patients, to predict unplanned readmission after discharge, and also for health monitoring of devices/machines, etc. With various parameters being recorded over a period of time in databases, Recurrent Neural Networks (RNNs) can be an effective way to model the sequential aspects of EHR data, e.g. diagnoses, mortality prediction and estimating length of stay, and fault diagnostics from sensor data from machines and the like. However, training RNNs requires large labeled training data like any other deep learning approach, and can be computationally inefficient because of sequential nature of computations.

SUMMARY

Embodiments of the present disclosure present technological improvements as solutions to one or more of the above-mentioned technical problems recognized by the inventors in conventional systems. For example, in one aspect, there is provided a processor implemented method for classifying multi-dimensional time series of parameters. The method comprises obtaining a plurality of unique time series data corresponding to a plurality of parameters of one or more entities, wherein each unique time series data comprises one or more time series data corresponding each parameter of the plurality of parameters, and wherein the unique time series data is a fixed length data or a variable length data; automatically extracting, using an unsupervised encoder integrated within a Deep Recurrent Neural Network (RNN), one or more features from the unique time series to obtain a unique features set for each of the plurality of parameters, wherein the unique features set comprises a fixed-dimensional feature vector; concatenating features from the unique features set pertaining each of the plurality of parameters to obtain a concatenated features set comprising a fixed-dimensional concatenated feature vector; learning a non-temporal linear classification model based on the concatenated features set, wherein during the learning of the non-temporal linear classification model a weight is assigned to each feature from the concatenated features set, and wherein the weight is obtained using a LASSO-regularized loss function (also referred as "Least Absolute Shrinkage and Selection Operator-regularized loss function"); and generating a relevance score for each of the plurality of parameters based on the weight of each feature from the concatenated features set to validate the learned non-temporal linear classification model.

In an embodiment, the method may further comprise receiving an input time series corresponding to the plurality of parameters of the entity; automatically extracting one or more features from the input time series; and applying the validated learned classification model on the input time series based on the extracted one or more features to obtain a class for the input time series corresponding to the plurality of parameters of the entity.

In one aspect, there is provided a processor implemented system for classifying multi-dimensional time series of parameters. The system comprises: a memory storing instructions; one or more communication interfaces; and one or more hardware processors coupled to the memory via the one or more communication interfaces, wherein the one or more hardware processors are configured by the instructions to: obtain a unique time series data corresponding to a plurality of parameters of an entity; automatically extract, using an unsupervised encoder integrated within a Deep Recurrent Neural Network (RNN) implemented by the system, one or more features from the unique time series to obtain a unique features set for each of the plurality of parameters, wherein the unique features set comprises a fixed-dimensional feature vector; concatenate features from the unique features set pertaining each of the plurality of parameters to obtain a concatenated features set comprising a fixed-dimensional concatenated feature vector; learn a non-temporal linear classification model based on the concatenated features set, wherein during the learning of the non-temporal linear classification model a weight is assigned to each feature from the concatenated features set, and wherein the weight is obtained using a LASSO-regularized loss function (also referred as "Least Absolute Shrinkage and Selection Operator-regularized loss function"); and generate a relevance score for each of the plurality of parameters based on the weight of each feature from the concatenated features set to validate the learned non-temporal linear classification model.

In an embodiment, the one or more hardware processors are further configured to: receive an input time series corresponding to the plurality of parameters of the entity; automatically extract one or more features from the input time series; apply the validated learned classification model on the input time series based on the extracted one or more features to obtain a class for the input time series corresponding to the plurality of parameters of the entity.

In an embodiment, the input time series and the unique time series data is a fixed length data or a variable length data.

In yet another aspect, there are provided one or more non-transitory machine readable information storage mediums comprising one or more instructions which when executed by one or more hardware processors causes classifying multi-dimensional time series of parameters by obtaining a unique time series data corresponding to a plurality of parameters of an entity, wherein the unique time series data is a fixed length data or a variable length data; automatically extracting, using an unsupervised encoder integrated within a Deep Recurrent Neural Network (RNN), one or more features from the unique time series to obtain a unique features set for each of the plurality of parameters, wherein the unique features set comprises a fixed-dimensional feature vector; concatenating features from the unique features set pertaining each of the plurality of parameters to obtain a concatenated features set comprising a fixed-dimensional concatenated feature vector; learning a non-temporal linear classification model based on the concatenated features set, wherein during the learning of the non-temporal linear classification model a weight is assigned to each feature from the concatenated features set, and wherein the weight is obtained using a LASSO-regularized loss function (also referred as "Least Absolute Shrinkage and Selection Operator-regularized loss function"); and generating a relevance score for each of the plurality of parameters based on the weight of each feature from the concatenated features set to validate the learned non-temporal linear classification model.

In an embodiment, the instructions when executed by the one or more hardware processors may further cause receiving an input time series corresponding to the plurality of parameters of the entity; automatically extracting one or more features from the input time series; and applying the validated learned classification model on the input time series based on the extracted one or more features to obtain a class for the input time series corresponding to the plurality of parameters of the entity.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
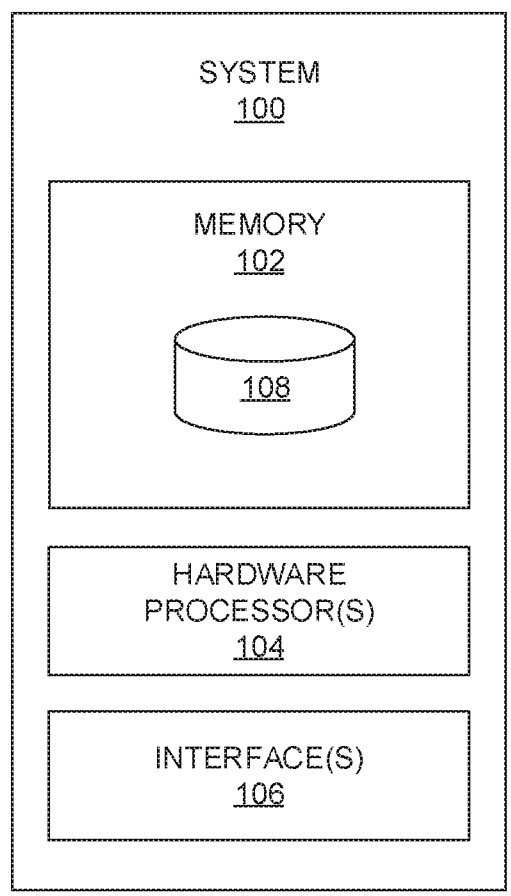
FIG. 1 illustrates an exemplary block diagram of a system for classifying multi-dimensional time series of parameters of entities in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Training a deep network on diverse instances can provide generic features for unseen instances, e.g., VGGNet for images. Also, fine-tuning a pre-trained network with transfer learning is often faster and easier than constructing and training a new network from scratch. The advantage of learning in such a manner is that the pre-trained network has already learned a rich set of features that can then be applied to a wide range of other similar tasks.

In the present disclosure, embodiments and systems and methods associated thereof provide an efficient way to learn prediction models for clinical time series by leveraging general purpose features via TimeNet. TimeNet maps variable-length time series (say clinical time series) to fixed-dimensional feature vectors that are subsequently used for classification (e.g., patient phenotyping and in-hospital mortality prediction tasks on MIMIC-III database) via easily trainable non-temporal linear classification models. It is observed by the present disclosure that TimeNet-based features can be used to build such classification models with very little training effort while yielding performance comparable to models with hand-crafted features or carefully trained domain specific RNNs. The present disclosure further proposes to leverage the weights of the linear classification models to provide insights into the relevance of each raw input parameter.

Referring now to the drawings, and more particularly to FIGS. 1 through 4B, where similar reference characters denote corresponding features consistently throughout the figures, there are shown preferred embodiments and these embodiments are described in the context of the following exemplary system and/or method.

FIG. 1 illustrates an exemplary block diagram of a system 100 for classifying multi-dimensional time series of parameters of entities in accordance with an embodiment of the present disclosure. In an embodiment, the system 100 may also be referred as 'a classification system', and interchangeably used hereinafter. In an embodiment, the system 100 includes one or more processors 104, communication interface device(s) or input/output (I/O) interface(s) 106, and one or more data storage devices or memory 102 operatively coupled to the one or more processors 104. The memory 102 comprises a database 108. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

The database 108 may store information but are not limited to, a plurality of parameters obtained from one or more sensors, wherein the parameters are specific to entities (e.g., user, machine, and the like). Parameters may comprise sensor data captured through the sensors either connected to the user(s) and/or machine(s). Further, the database 108 stores information pertaining to inputs fed to the system 100 and/or outputs generated by the system (e.g., at each stage), specific to the methodology described herein. More specifically, the database 108 stores information being processed at each step of the proposed methodology.

Figure 2:
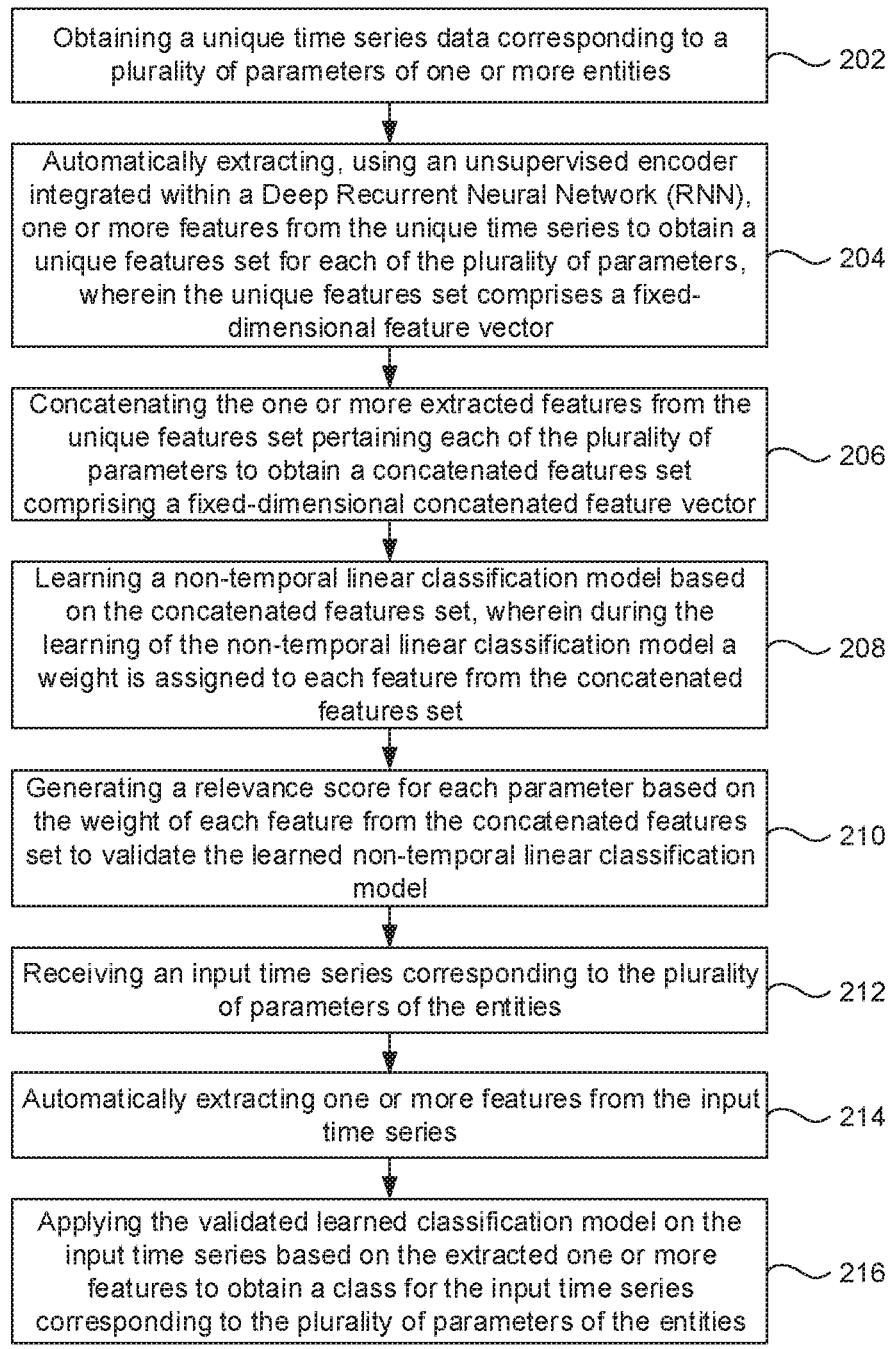
FIG. 2 illustrates an exemplary flow diagram illustrating a method for classifying multi-dimensional time series of parameters using the system of FIG. 1 according to an embodiment of the present disclosure.
Figure 3A:
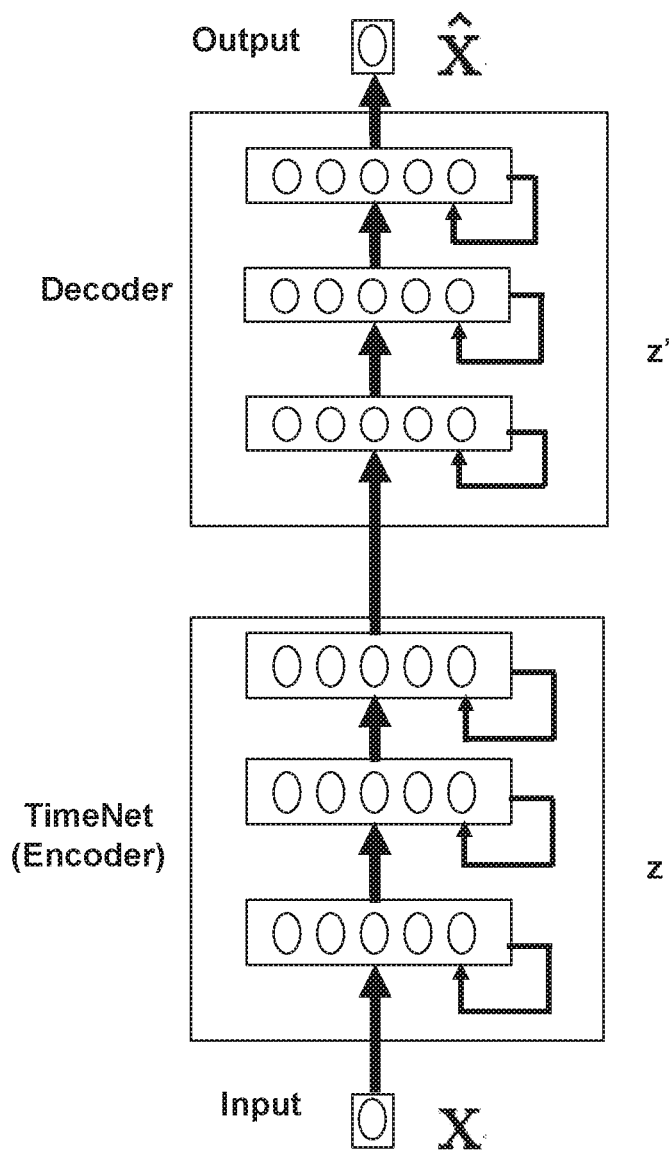
FIG. 3A depicts TimeNet trained via RNN Encoder-Decoder with three hidden Gated Recurrent Unit (GRU) layers implemented by the system of FIG. 1 in accordance with an example embodiment of the present disclosure.

FIG. 2, with reference to FIG. 1, illustrates an exemplary flow diagram illustrating a method for classifying multi-dimensional time series of parameters using the system 100 of FIG. 1 according to an embodiment of the present disclosure. In an embodiment, the system 100 comprises one or more data storage devices or the memory 102 operatively coupled to the one or more hardware processors 104 and is configured to store instructions for execution of steps of the method by the one or more processors 104. TimeNet is a pre-trained off-the-shelf feature extractor for univariate time series with three recurrent layers having say 60 Gated Recurrent Units (GRUs) each. TimeNet is an RNN trained via an autoencoder consisting of an encoder RNN and a decoder RNN trained simultaneously using a sequence-to-sequence learning framework as shown in FIG. 3A. More specifically, FIG. 3A, with reference to FIGS. 1 through 2, depicts TimeNet trained via RNN Encoder-Decoder with three hidden GRU layers implemented by the system 100 of FIG. 1 in accordance with an example embodiment of the present disclosure. RNN autoencoder is trained to obtain the parameters $W_E$ of the encoder RNN $f_E$ via reconstruction task such that for input $x_1 \ldots T = x_1, x_2 \ldots, x_T (x_i \in \mathbb{R})$ the target output time series $x_T \ldots 1 = x_T, x_{T-1} \ldots, x_1$ is reverse of the input. The RNN encoder $f_E$ provides a non-linear mapping of the multi-variate input time series to a fixed-dimensional vector representation $z_T$: $z_T = f_E(x_1 \ldots T; W_E)$, followed by an RNN decoder $f_D$ based non-linear mapping of $z_T$ to multi-variate time series $\hat{x}_{T \ldots 1} = f_D(z_T; W_D)$; where $W_E$ and $W_D$ are the parameters of the encoder and decoder, respectively. The model is trained to minimize the average squared reconstruction error. Training on several diverse datasets simultaneously results in robust time series features getting captured in $z_T$: the decoder relies on $z_T$ as the only input to reconstruct the time series, forcing the encoder to capture all the relevant information in the time series into the fixed-dimensional vector $z_T$. This vector $z_T$ is used as the feature vector for input $x_1 \ldots T$. This feature vector is then used to train a simpler classifier (e.g., Support Vector Machine (SVM)) for the end task. TimeNet maps a multi-variate input time series to 180-dimensional feature vector, where each dimension corresponds to final output of one of the 60 GRUs in the 3 recurrent layers.

The steps of the method of the present disclosure will now be explained with reference to the components of the system 100 as depicted in FIG. 1, and the flow diagram of FIG. 2. In an embodiment of the present disclosure, at step 202, the one or more hardware processors 104 obtain a unique time series data corresponding to a plurality of parameters of one or more entities (e.g., in this case entities can be a user, or a machine, and the like). In an embodiment, the plurality of parameters are obtained from one or more sensors, for example, temperature sensor, motion sensor, health monitoring sensor(s), and the like. In an embodiment, the one or more entities can also be referred as 'entities' and interchangeably used hereinafter. Each unique time series data comprises one or more time series data corresponding to each parameter of the plurality of parameters. The one or more time series data cumulatively constitutes a unique time series data that is obtained as input to the system prior to performing feature extraction. Therefore there can be multiple unique time series data (UTSD 1, UTSD 2, UTSD 3 and so on) fed as input to the system 100, wherein each of the multiple unique time series data is specific to a corresponding parameter and an entity respectively. For instance, UTSD 1 comprises one or more time series data (says TSD 1, TSD 2, TSD 3 and so on) corresponding to parameters (say P1, P2, P3 and so on) of an entity say E1. Similarly, another unique time series data (say UTSD 2) comprises one or more time series data (says TSD 11, TSD 12, TSD 13 and so on) corresponding to parameters (say P1, P2, P3, and so on) of another entity say E2. In an embodiment of the present disclosure, at step 204, the one or more hardware processors 104 automatically extract, using an unsupervised encoder integrated within a Deep Recurrent Neural Network (RNN), one or more features from the unique time series to obtain a unique features set for each of the plurality of parameters, wherein the unique features set comprises a fixed-dimensional feature vector. For a multivariate time series $x = x_1 x_2 \ldots x_T$ where $x_T \in \mathbb{R}^n$, the system 100 considers time series for each of the n raw input parameters (e.g., physiological parameters such as glucose level, heart rate, etc.) independently to obtain univariate time series $x_j = x_{j1} x_{j2} \ldots x_{jT}$, $j=1 \ldots n$. The system further obtains a vector representation $z_{jT} = f_E(x_j; W_E)$ for $x_j$, where $z_{jT} \in \mathbb{R}^c$ using TimeNet as $f_E$ with c=180 (as described in later section). In general, time series length T also depends on i, e.g., based on length of stay in hospital. The system 100 further converts each time series to have equal length T by suitable pre/post padding with 0s. In other words, the unique features set comprises a fixed dimensional feature vector.

Figure 3B:
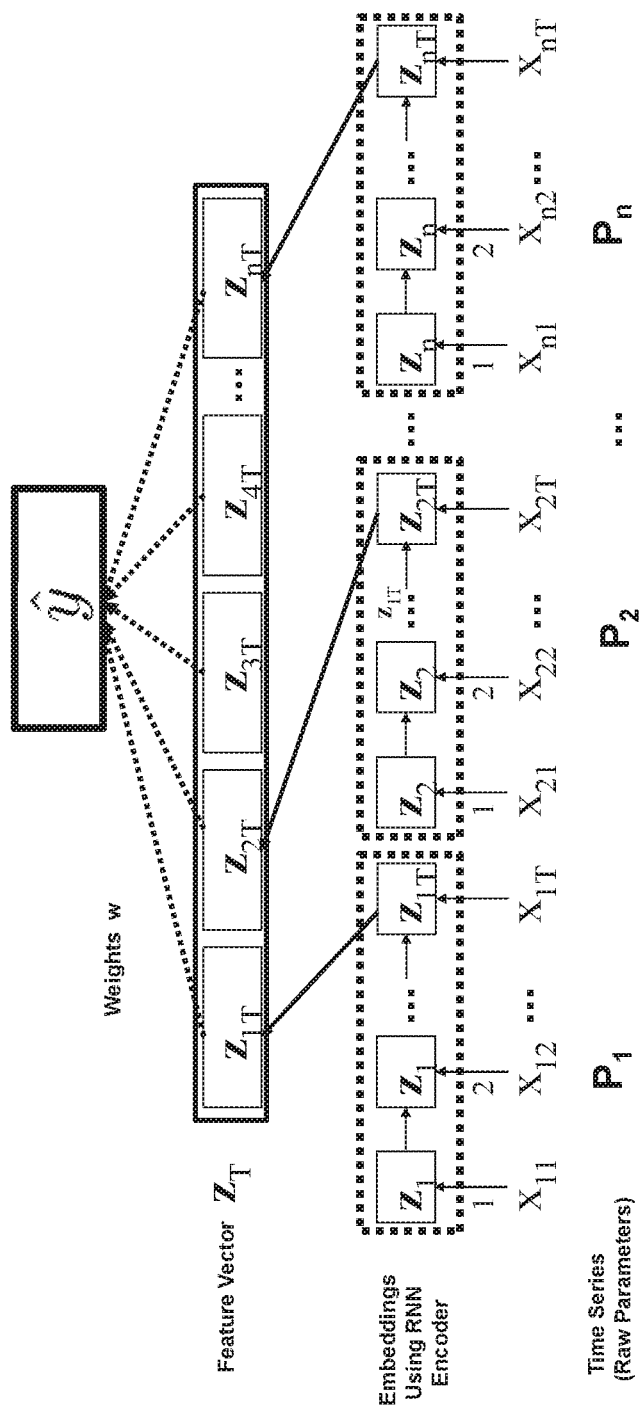
FIG. 3B depicts TimeNet based feature extraction as implemented by the system of FIG. 1 in accordance with an example embodiment of the present disclosure.

In an embodiment of the present disclosure, at step 206, the one or more hardware processors 104 concatenate features from the unique features set pertaining each of the plurality of parameters to obtain a concatenated features set comprising a fixed-dimensional concatenated feature vector. In other words, the system 100 concatenates the TimeNet-features $z_{jT}$ for each raw input parameter j to get the final feature vector $z_T = [z_{1T}, z_{2T}, \ldots, z_{nT}]$ for time series x which is also a fixed dimensional concatenated feature vector, where $z_T \in \mathbb{R}^c$, m=n×c as illustrated in FIG. 3B. More specifically, FIG. 3B, with reference to FIGS. 1 through 3A, depicts TimeNet based Feature Extraction as implemented by the system 100 of FIG. 1 in accordance with an example embodiment of the present disclosure.

In an embodiment of the present disclosure, at step 208, the one or more hardware processors 104 learn a non-temporal linear classification model based on the concatenated features set, wherein during the learning of the non-temporal linear classification model a weight is assigned to each feature from the concatenated features set. In other words, the final concatenated feature vector $z_T$ is used as input for the classification tasks (e.g., say phenotyping and mortality prediction classification tasks in case of physiological parameters). As discussed above, since c=180 is large, $z_T$ has large number of features m≥180. Mapping from input TimeNet features $z_T$ to the target label y is considered such that the estimate $\hat{y}=w \cdot z_T$, where $w \in \mathbb{R}^m$. The system 100 constrains the non-temporal linear model with weights w to use only a few of these large number of features. In an embodiment the weight is obtained using a LASSO-regularized loss function (also referred as "Least Absolute Shrinkage and Selection Operator-regularized loss function") expressed by way of following example below:

$$\arg\min_w \frac{1}{N} \sum_{i=1}^{N} (y^{(i)} - w \cdot z_T^{(i)})^2 + \alpha \|w\|_1 \tag{1}$$

where $y^{(i)} \in \{0,1\}$, $\|w\|_1 = \sum_{j=1}^{n} \sum_{k=1}^{c} |w_{jk}|$ is the $L_1$-norm, where $w_{jk}$ represents the weight assigned to the k-th Time-Net feature for the j-th raw input parameter, and $\alpha$ controls the extent of sparsity—with higher $\alpha$ implying more sparsity, i.e., fewer TimeNet features are selected for the final classifier.

In an embodiment of the present disclosure, at step 210, the one or more hardware processors 104 generate a relevance score for each of the plurality of parameters based on the weight of each feature from the concatenated features set to validate the learned non-temporal linear classification model. In an embodiment of the present disclosure validation of learned non-temporal linear classification model includes (i) validating the incoming time series, (ii) validating feature extraction and associated output thereof, (iii) validating the concatenating process and output generated thereof thereby validating the learned non-temporal linear classification model itself.

Figure 3C:
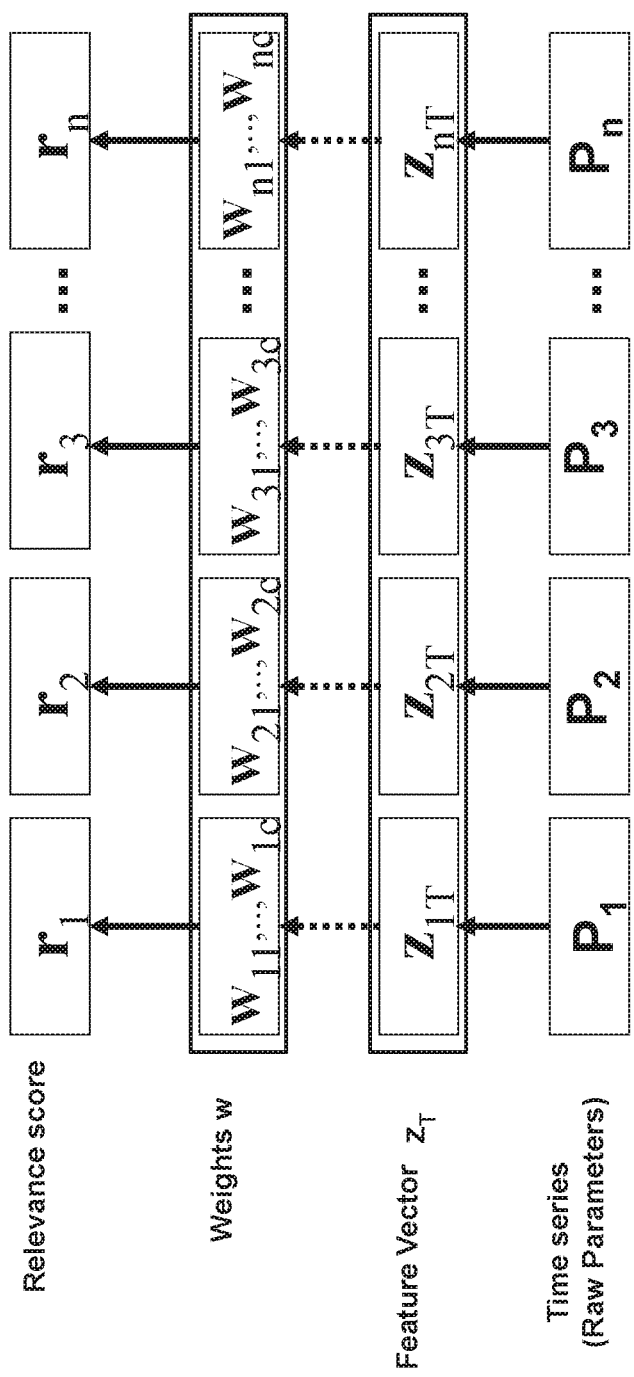
FIG. 3C depicts generation of relevance scores for raw input parameters using the system of FIG. 1 in accordance with an example embodiment of the present disclosure.

The above relevance score generation is described below by way of example below:

Determining relevance of the n raw input parameter for a given phenotype is potentially useful to obtain insights into the obtained classification model. The sparse weights w are easy to interpret and can give interesting insights into relevant parameters for a classification task. In the present disclosure, the system 100 generates relevance score say $r_j$ for j-th raw input parameter as the sum of absolute values of the weights $w_{jk}$ assigned to the corresponding TimeNet features $z_{jT}$ as shown in FIG. 3C. More specifically, FIG. 3C, with reference to FIGS. 1 through 3B, depicts generation of relevance scores for raw input parameters using the system 100 of FIG. 1 in accordance with an example embodiment of the present disclosure. Here, T is time series length, n is number of raw input parameters. The relevance score is generated by way of following example expression below:

$$r_j = \sum_{k=1}^{c} |w_{jk}|, j=1 \ldots n. \tag{2}$$

Further, $r_j$ is normalized using min-max normalization such that $$r'_j = \frac{r_j - r_{min}}{r_{max} - r_{min}} \in [0,1];$$

$r_{min}$ is minimum of $\{r_1, \ldots, r_n\}$, $r_{max}$ is maximum of $\{r_1, \ldots, r_n\}$. In practice, this kind of relevance score generation for the raw input parameter help to interpret and validate the learned non-temporal linear classification model as described above. For example, one would expect glucose level feature to have a high relevance score when learning a model to detect diabetes mellitus phenotype.

Upon obtaining the overall interpretable learned classification model (post validation), the system 100 further implements this interpretable classification model on a test input data wherein an input time series corresponding to the plurality of parameters of the entities is received and one or more features are automatically extracted from the input time series. The system 100 then applies the validated learned classification model on the input time series based on the extracted one or more features to obtain a class for the input time series corresponding to the plurality of parameters of the entities. In an embodiment of the present disclosure, both during the training phase (or during learning of the classification model) and the testing phase, input time series that is received by the system 100 may be a fixed length data or a variable length data.

Experimental Evaluation:

In the present disclosure, MIMIC-Ill (v1.4) clinical database was used [e.g., refer 'Alistair E W Johnson, Tom J Pollard, Lu Shen, H Lehman Li-wei, Mengling Feng, Mohammad Ghassemi, Benjamin Moody, Peter Szolovits, Leo Anthony Celi, and Roger G Mark. Mimic-iii, a freely accessible critical care database. Scientific data, 3:160035, 2016'] which consisted of over 60,000 ICU stays across 40,000 critical care patients]. An experimental setup was implemented with certain number of splits, train, validation and test datasets (e.g., refer 'https://github.com/yerevann/mimic3-benchmarks') based on 17 physiological time series with 12 real-valued and 5 categorical time series, sampled at 1 hour intervals. The categorical variables were converted to (one-hot) vectors such that final multivariate time series has n=76 raw input parameters (59 actual parameters and 17 masking parameters to denote missing values).

For phenotyping task, the goal was to classify 25 phenotypes common in adult ICUs. For in-hospital mortality task, the goal was to predict whether the patient survives or not given the time series observations up to 48 hours. In all experiments performed by the systems and methods of the present disclosure, training time series data was restricted up to first 48 hours in ICU stay, such that T=48 hours while training all models to imitate practical scenario where early predictions are important, unlike conventional researches (or technique) (e.g., refer conventional method 1 "Harutyunyan et al., 2017—Hrayr Harutyunyan, Hrant Khachatrian, David C Kale, and Aram Galstyan. Multitask learning and benchmarking with clinical time series data. arXiv preprint arXiv: 1703.07771, 2017" and conventional method 2—"Song et al., 2017—Huan Song, Deepta Rajan, Jayaraman J Thiagarajan, and Andreas Spanias. Attend and diagnose: Clinical time series analysis using attention models. arXiv preprint arXiv:1711.03905, 2017") which used entire time series for training the classifier for phenotyping task.

Evaluation:

The present disclosure had n=76 raw input parameters resulting in m=13,680-dimensional (m=76×180) TimeNet feature vector for each admission. The systems and methods of the present disclosure used $\alpha$=0.0001 for phenotype classifiers and $\alpha$=0.0003 for in-hospital mortality classifier ($\alpha$ was chosen based on hold-out validation set). Below Table 1 summarizes the results and provides comparison with existing/traditional benchmarks. Table 2 describes detailed phenotype-wise results.

TABLE 1

| | Conventional method 1 | | | Conventional method 2 | | Proposed method | | | |
|---|---|---|---|---|---|---|---|---|---|
| Metric | LR | LSTM | LSTM-multi | SAnD | SAnD multi | TimeNet (TN) 48 | TimeNet (TN) All | TN 48 Eps | TN-All Eps* |
| Task 1 | | | | | Phenotyping | | | | |
| Micro AUC | 0.801 | 0.821 | 0.817 | 0.816 | 0.819 | 0.812 | 0.813 | 0.820 | 0.822 |
| Macro AUC | 0.741 | 0.77 | 0.766 | 0.766 | 0.771 | 0.761 | 0.764 | 0.772 | 0.775 |
| Weighted AUC | 0.732 | 0.757 | 0.753 | 0.754 | 0.759 | 0.751 | 0.754 | 0.765 | 0.768 |
| Task 2 | | | | | In-Hospital Mortality Prediction** | | | | |
| AUROC | 0.845 | 0.854 | 0.863 | 0.857 | 0.859 | 0.852 | — | — | — |
| AUPRC | 0.472 | 0.516 | 0.517 | 0.518 | 0.519 | 0.519 | — | — | — |
| min(Se, +P) | 0.469 | 0.491 | 0.499 | 0.5 | 0.504 | 0.486 | — | — | — |

In above Table 1, LR refers to Logistic regression, LSTM-Multi refers to LSTM-based multitask model, SAnD refers to (Simply Attend and Diagnose): Fully attention-based model, SAnD-Multi refers to SAnD-based multitask model. (Note: *For phenotyping, the present disclosure and associated systems and methods thereof compare TimeNet-48-Eps with existing/conventional or traditional benchmarks over TimeNet-All-Eps as it is more applicable in practical scenarios. **Only TimeNet-48 variant is applicable for in-hospital mortality task.)

TABLE 2

| Sl. No | Phenotype | LSTM-Multi | TimeNet-48 | TimeNet-All | TimeNet-48-Eps | TimeNet-All-Eps |
|---|---|---|---|---|---|---|
| 1 | Acute and unspecified renal failure | 0.8035 | 0.7861 | 0.7887 | 0.7912 | 0.7941 |
| 2 | Acute cerebrovascular disease | 0.9089 | 0.8989 | 0.9031 | 0.8986 | 0.9033 |
| 3 | Acute myocardial infarction | 0.7695 | 0.7501 | 0.7478 | 0.7533 | 0.7509 |
| 4 | Cardiac dysrhythmias | 0.684 | 0.6853 | 0.7005 | 0.7096 | 0.7239 |
| 5 | Chronic kidney disease | 0.7771 | 0.7764 | 0.7888 | 0.7960 | 0.8061 |
| 6 | Chronic obstructive pulmonary disease and bronchiectasis | 0.6786 | 0.7096 | 0.7236 | 0.7460 | 0.7605 |
| 7 | Complications of surgical procedures or medical care | 0.7176 | 0.7061 | 0.6998 | 0.7092 | 0.7029 |
| 8 | Conduction disorders | 0.726 | 0.7070 | 0.7111 | 0.7286 | 0.7324 |
| 9 | Congestive heart failure; non-hypertensive | 0.7608 | 0.7464 | 0.7541 | 0.7747 | 0.7805 |
| 10 | Coronary atherosclerosis and other heart disease | 0.7922 | 0.7764 | 0.7760 | 0.8007 | 0.8016 |
| 11 | Diabetes mellitus with complications | 0.8738 | 0.8748 | 0.8800 | 0.8856 | 0.8887 |
| 12 | Diabetes mellitus without complication | 0.7897 | 0.7749 | 0.7853 | 0.7904 | 0.8000 |
| 13 | Disorders of lipid metabolism | 0.7213 | 0.7055 | 0.7119 | 0.7217 | 0.7280 |
| 14 | Essential hypertension | 0.6779 | 0.6591 | 0.6650 | 0.6757 | 0.6825 |
| 15 | Fluid and electrolyte disorders | 0.7405 | 0.7351 | 0.7301 | 0.7377 | 0.7328 |
| 16 | Gastrointestinal hemorrhage | 0.7413 | 0.7364 | 0.7309 | 0.7386 | 0.7343 |

TABLE 2-continued

| Sl. No | Phenotype | LSTM-Multi | TimeNet-48 | TimeNet-All | TimeNet-48-Eps | TimeNet-All-Eps |
|---|---|---|---|---|---|---|
| 17 | Hypertension with complications and secondary hypertension | 0.76 | 0.7606 | 0.7700 | 0.7792 | 0.7871 |
| 18 | Other liver diseases | 0.7659 | 0.7358 | 0.7332 | 0.7573 | 0.7530 |
| 19 | Other lower respiratory disease | 0.688 | 0.6847 | 0.6897 | 0.6896 | 0.6922 |
| 20 | Other upper respiratory disease | 0.7599 | 0.7515 | 0.7565 | 0.7595 | 0.7530 |
| 21 | Pleurisy; pneumothorax; pulmonary collapse | 0.7027 | 0.6900 | 0.6882 | 0.6909 | 0.6997 |
| 22 | Pneumonia | 0.8082 | 0.7857 | 0.7916 | 0.7890 | 0.7943 |
| 23 | Respiratory failure; insufficiency; arrest (adult) | 0.9015 | 0.8815 | 0.8856 | 0.8834 | 0.8876 |
| 24 | Septicemia (except in labor) | 0.8426 | 0.8276 | 0.8140 | 0.8296 | 0.8165 |
| 25 | Shock | 0.876 | 0.8764 | 0.8564 | 0.8763 | 0.8562 |

As can be seen in the above tables (Table 1 and Table 2), in the present disclosure, two variants of classifier models were considered for phenotyping task: i) TimeNet-x using data from current episode, ii) TimeNet-x-Eps using data from previous episode of a patient as well (whenever available) via an additional input feature related to presence or absence of the phenotype in previous episode. Each classifier was trained using up to first 48 hours of data after ICU admission. However, two classifier variants were considered depending upon hours of data x used to estimate the target class at test time. For x=48, data up to first 48 hours after admission is used for determining the phenotype. For x=All, the learned classifier was applied to all 48-hours windows (overlapping with shift of 24 hours) over the entire ICU stay period of a patient, and the average phenotype probability across windows was used as the final estimate of the target class. In TimeNet-x-Eps, the additional feature is related to the presence (1) or absence (0) of the phenotype during the previous episode. The ground-truth value for this feature was used during training time, and the probability of presence of phenotype during previous episode (as given via LASSO-based classifier (also referred as "Least Absolute Shrinkage and Selection Operator-regularized loss function") at test time.

Table 3 depicts a list of input parameters pertaining to a user (in this case physiological parameters) as below:

TABLE 3

| 1 | Glucose |
|---|---|
| 2 | Glasgow coma scale total → 7 |
| 3 | Glasgow coma scale verbal response → Incomprehensible sounds |
| 4 | Diastolic blood pressure |
| 5 | Weight |
| 6 | Glasgow coma scale total → 8 |
| 7 | Glasgow coma scale motor response → Obeys Commands |

TABLE 3-continued

| 8 | Glasgow coma scale eye opening → None |
|---|---|
| 9 | Glasgow coma scale eye opening → To pain |
| 10 | Glasgow coma scale total → 6 |
| 11 | Glasgow coma scale verbal response → 1.0 ET/Trach |
| 12 | Glasgow coma scale total → 5 |
| 13 | Glasgow coma scale verbal response → 5 Oriented |
| 14 | Glasgow coma scale total → 3 |
| 15 | Glasgow coma scale verbal response → No Response |
| 16 | Glasgow coma scale motor response → 3 Abnorm flexion |
| 17 | Glasgow coma scale verbal response → 3 Inapprop words |
| 18 | Capillary refill rate → 1.0 |
| 19 | Glasgow coma scale verbal response → Inappropriate Words |
| 20 | Systolic blood pressure |
| 21 | Glasgow coma scale motor response → Flex-withdraws |
| 22 | Glasgow coma scale total → 10 |
| 23 | Glasgow coma scale motor response → Obeys Commands |
| 24 | Glasgow coma scale verbal response → No Response-ETT |
| 25 | Glasgow coma scale eye opening → 2 To pain |
| 26 | Heart Rate |
| 27 | Respiratory rate |

TABLE 3-continued

| | |
|---|---|
| 28 | Glascow coma scale verbal response → Oriented |
| 29 | Glascow coma scale motor response → Localizes Pain |
| 30 | Temperature |
| 31 | Glascow coma scale eye opening → 3 To speech |
| 32 | Height |
| 33 | Glascow coma scale motor response → 5 Localizes Pain |
| 34 | Glascow coma scale total → 14 |
| 35 | Fraction inspired oxygen |
| 36 | Glascow coma scale total → 12 |
| 37 | Glascow coma scale verbal response → Confused |
| 38 | Glascow coma scale motor response → 1 No response |
| 39 | Mean blood pressure |
| 40 | Glascow coma scale total → 4 |
| 41 | Glascow coma scale eye opening → To Speech |
| 42 | Glascow coma scale total → 15 |
| 43 | Glascow coma scale motor response → 4 Flex-withdraws |
| 44 | Glascow coma scale motor response → No response |
| 45 | Glascow coma scale eye opening → Spontaneously |
| 46 | Glascow coma scale verbal response → 4 Confused |
| 47 | Capillary refill rate → 0.0 |
| 48 | Glascow coma scale total → 13 |
| 49 | Glascow coma scale eye opening → 1 No Response |
| 50 | Glascow coma scale motor response → Abnormal extension |
| 51 | Glascow coma scale total → 11 |
| 52 | Glascow coma scale verbal response → 2 Incomp sounds |
| 53 | Glascow coma scale total → 9 |
| 54 | Glascow coma scale motor response → Abnormal Flexion |
| 55 | Glascow coma scale verbal response → 1 No Response |
| 56 | Glascow coma scale motor response → 2 Abnorm extensn |
| 57 | pH |
| 58 | Glascow coma scale eye opening → 4 Spontaneously |
| 59 | Oxygen saturation |

Observation(s):

Classification Task(s):

For the phenotyping task, following observations were made from Table 1:

TimeNet-48 vs LR: TimeNet-based features perform significantly better than hand-crafted features as used in LR (logistic regression), while using first 48 hours of data only unlike the LR approach that uses entire episode's data. This proves the effectiveness of TimeNet features for MIMIC-III data. Further, it only requires tuning a single hyper-parameter for LASSO, unlike other approaches like LSTM (e.g., refer convention method 1) that would involve tuning number of hidden units, layers, learning rate, etc.

TimeNet-x vs TimeNet-x-Eps: Leveraging previous episode's time series data for a patient significantly improves the classification performance.

TimeNet-48-Eps performs better than existing/conventional (or traditional) benchmarks, while still being practically more feasible as it looks at only up to 48 hours of current episode of a patient rather than the entire current episode. For in-hospital mortality task, as depicted in above Table 2, a comparable performance was observed when compared to existing benchmarks.

Training linear models is significantly fast and it took around 30 minutes for obtaining any of the binary classifiers while tuning for $\alpha \in [10^{-5}-10^{-3}]$ (five equally-spaced values) on a 32 GB RAM machine with Quad Core i7 2.7 GHz processor. It was observed that LASSO leads to 91.2±0.8% sparsity (i.e., percentage of weights $w_{jk} \approx 0$) for all classifiers leading to around 550 useful features (out of 13,680) for each phenotype classification.

Figure 4A:
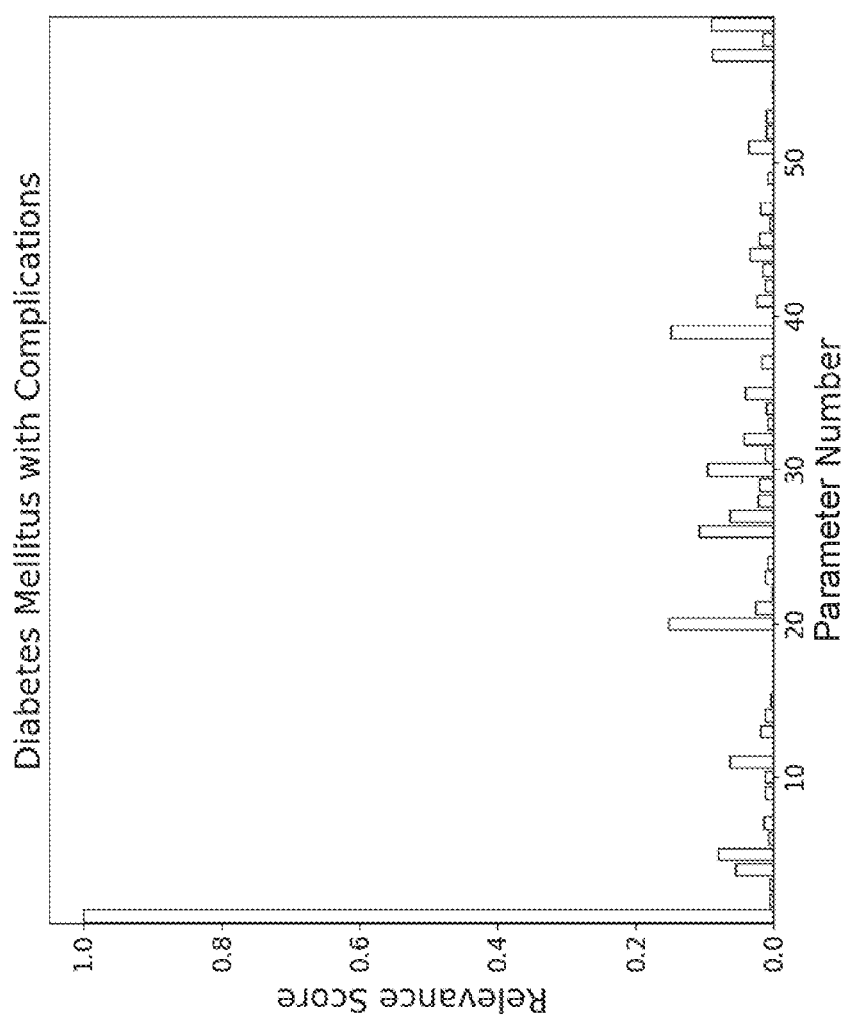
FIG. 4A depicts a graphical representation illustrating highest relevance score obtained for Glucose Level (parameter 1) for phenotype Diabetes Mellitus with Complications in accordance with an embodiment of the present disclosure.
Figure 4B:
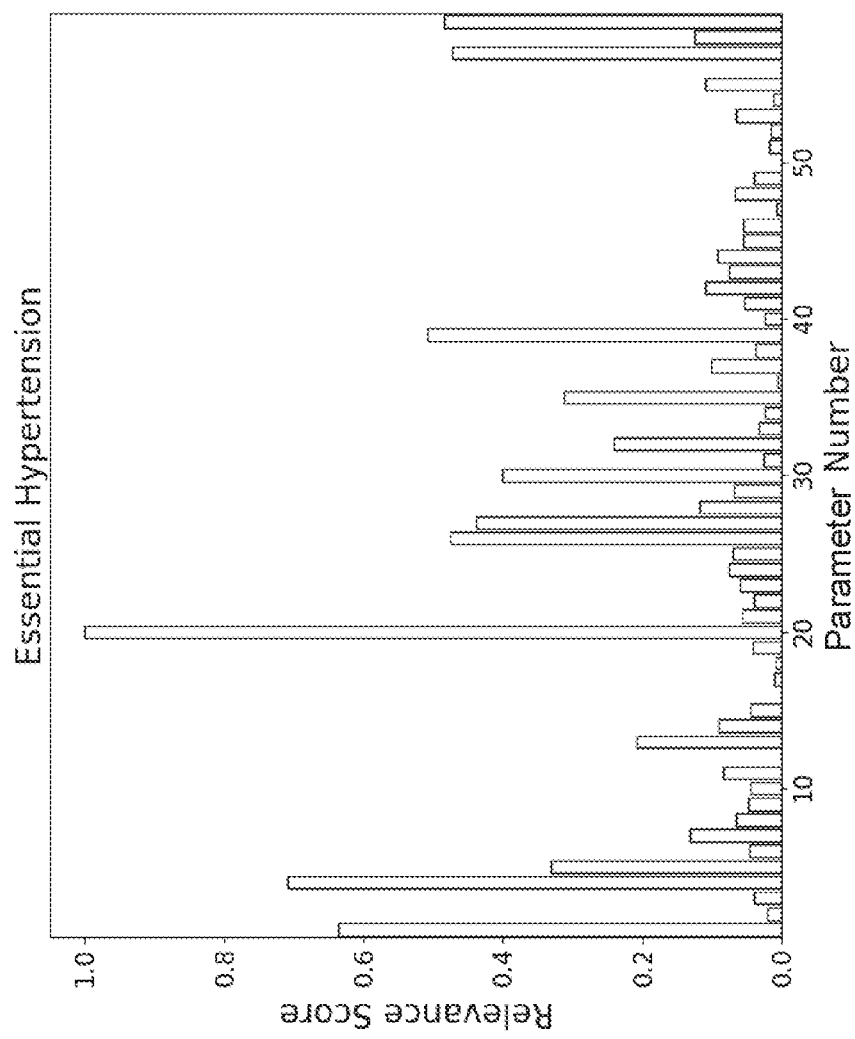
FIG. 4B depicts a graphical representation illustrating highest relevance scores obtained for Systolic Blood Pressure (parameter 20) for phenotype Essential Hypertension in accordance with an embodiment of the present disclosure.

Relevance Score for Raw Input Parameters:

Intuitive interpretation for relevance of raw input parameters was observed using the weights assigned to various TimeNet features (refer Equation 2): For example, as shown in FIGS. 4A-4B, highest relevance scores were obtained for Glucose Level (parameter 1) and Systolic Blood Pressure (parameter 20) for Diabetes Mellitus with Complications (FIG. 4A), and Essential Hypertension (FIG. 4B), respectively. More specifically, FIG. 4A, with reference to FIGS. 1 through 3C, depicts a graphical representation illustrating highest relevance scores obtained for Glucose Level (parameter 1) for phenotype Diabetes Mellitus with Complications in accordance with an embodiment of the present disclosure. FIG. 4B, with reference to FIGS. 1 through 4A, depicts a graphical representation illustrating highest relevance scores obtained for and Systolic Blood Pressure (parameter 20) for phenotype Essential Hypertension in accordance with an embodiment of the present disclosure. As can be seen from the above experimental results, since the TimeNet encoder was pre-trained on time series from various domains taken from UCR Time Series Archive, it provided meaningful general-purpose features from time series of raw input parameters, and LASSO helps to select the most relevant ones for end-task by using labeled data. Further, extracting features using a deep recurrent neural network model for time series of each raw input parameter independently—rather than considering a multivariate time series—eventually allows to easily assign relevance scores to raw input parameters in the input domain, allowing a high-level basic model validation by domain-experts. It is to be noted that in the convention art of traditional systems non-linear transformations in Recurrent Neural Networks imply that the classification decisions and the classification models are not interpretable and difficult to validate which is overcome by the embodiments of the present disclosure and proposed systems and methods. Although the present disclosure describes example scenarios pertaining to electronic health records of user(s), it is to be understood by person having ordinary skill in the art and person skilled in the art that such examples shall not be construed as limiting the scope of the present disclosure to classification tasks.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method, comprising:
    obtaining, via one or more hardware processors, a unique time series data corresponding to a plurality of parameters of one or more entities (202);
    automatically extracting, using an unsupervised encoder integrated within a Deep Recurrent Neural Network (RNN) executed by the one or more hardware processors, one or more features from the unique time series to obtain a unique features set for each of the plurality of parameters, wherein the unique features set comprises a fixed-dimensional feature vector (204);
    concatenating the one or more extracted features from the unique features set pertaining each of the plurality of parameters to obtain a concatenated features set comprising a fixed-dimensional concatenated feature vector (206);
    learning a non-temporal linear classification model based on the concatenated features set, wherein during the learning of the non-temporal linear classification model a weight is assigned to each feature from the concatenated features set (208); and
    generating a relevance score for each of the plurality of parameters based on the weight of each feature from the concatenated features set to validate the learned non-temporal linear classification model (210).

2. The processor implemented method of claim 1, further comprising:
    receiving an input time series corresponding to the plurality of parameters of the entities (212);
    automatically extracting one or more features from the input time series (214); and
    applying the validated learned classification model on the input time series based on the extracted one or more features to obtain a class for the input time series corresponding to the plurality of parameters of the entities (216).

3. The processor implemented method of claim 2, wherein the input time series and the unique time series data are a fixed length data or a variable length data.

4. The processor implemented method of claim 1, wherein the weight is obtained using a Least Absolute Shrinkage and Selection Operator (LASSO)-regularized loss function.

5. One or more non-transitory machine readable information storage mediums comprising one or more instructions which when executed by one or more hardware processors cause classifying multi-dimensional time series of parameters by:
    obtaining, via one or more hardware processors, a unique time series data corresponding to a plurality of parameters of one or more entities;
    automatically extracting, using an unsupervised encoder integrated within a Deep Recurrent Neural Network (RNN) executed by the one or more hardware processors, one or more features from the unique time series to obtain a unique features set for each of the plurality of parameters, wherein the unique features set comprises a fixed-dimensional feature vector;

concatenating the one or more extracted features from the unique features set pertaining each of the plurality of parameters to obtain a concatenated features set comprising a fixed-dimensional concatenated feature vector;

learning a non-temporal linear classification model based on the concatenated features set, wherein during the learning of the non-temporal linear classification model a weight is assigned to each feature from the concatenated features set; and generating a relevance score for each of the plurality of parameters based on the weight of each feature from the concatenated features set to validate the learned non-temporal linear classification model.

6. The one or more non-transitory machine readable information storage mediums of claim 5, wherein the instructions which when executed by the one or more hardware processors further cause:

receiving an input time series corresponding to the plurality of parameters of the entities;

automatically extracting one or more features from the input time series; and applying the validated learned classification model on the input time series based on the extracted one or more features to obtain a class for the input time series corresponding to the plurality of parameters of the entities.

7. The one or more non-transitory machine readable information storage mediums of claim 6, wherein the input time series and the unique time series data are a fixed length data or a variable length data.

8. The one or more non-transitory machine readable information storage mediums of claim 5, wherein the weight is obtained using a Least Absolute Shrinkage and Selection Operator (LASSO)-regularized loss function.

9. A system comprising:
a memory (102) storing instructions;
one or more communication interfaces (106); and
one or more hardware processors (104) coupled to the memory (102) via the one or more communication interfaces (106), wherein the one or more hardware processors (104) are configured by the instructions to:

obtain a unique time series data corresponding to a plurality of parameters of one or more entities;

automatically extract, using an unsupervised encoder integrated within a Deep Recurrent Neural Network (RNN) implemented by the system 100, one or more features from the unique time series to obtain a unique features set for each of the plurality of parameters, wherein the unique features set comprises a fixed-dimensional feature vector;

concatenate the one or more extracted features from the unique features set pertaining each of the plurality of parameters to obtain a concatenated features set comprising a fixed-dimensional concatenated feature vector;

learn a non-temporal linear classification model based on the concatenated features set, wherein during the learning of the non-temporal linear classification model a weight is assigned to each feature from the concatenated features set; and generate a relevance score for each of the plurality of parameters based on the weight of each feature from the concatenated features set to validate the learned non-temporal linear classification model.

10. The system of claim 9, wherein the one or more hardware processors are further configured to:

receive an input time series corresponding to the plurality of parameters of the entities;

automatically extract one or more features from the input time series;

apply the validated learned classification model on the input time series based on the extracted one or more features to obtain a class for the input time series corresponding to the plurality of parameters of the entities.

11. The system of claim 9, wherein the input time series and the unique time series data are a fixed length data or a variable length data.

12. The system of claim 9, wherein the weight is obtained using a Least Absolute Shrinkage and Selection Operator (LASSO)-regularized loss function.

* * * * *